United States Patent [19]

Gardner, Jr. et al.

[11] Patent Number: 4,471,496
[45] Date of Patent: Sep. 18, 1984

[54] ARTICULATED EARMUFF-TO-HEADBAND ATTACHMENT CONSTRUCTION

[75] Inventors: Ross Gardner, Jr.; Robert Falco, both of Indianapolis, Ind.

[73] Assignee: Cabot Corporation, Boston, Mass.

[21] Appl. No.: 507,984

[22] Filed: Jun. 27, 1983

[51] Int. Cl.³ .............................................. A42B 1/06
[52] U.S. Cl. .......................................... 2/209; 2/423; 403/326; 403/361; 339/126 RS
[58] Field of Search ................... 403/361, 326, 2, 133, 403/135; 285/22, 2; 2/423, 209, DIG. 7; 339/126 RS

[56] References Cited

U.S. PATENT DOCUMENTS

| | | | |
|---|---|---|---|
| 2,921,808 | 10/1959 | David | 403/133 |
| 2,999,708 | 10/1957 | Dudash | 403/135 |
| 3,222,093 | 12/1965 | Simmons | 285/DIG. 22 |
| 3,262,721 | 7/1966 | Knight | 285/DIG. 22 |
| 3,268,650 | 8/1966 | Nepker | 339/126 RS |
| 3,476,421 | 11/1969 | Torres | 403/326 |
| 3,815,155 | 6/1974 | Davison et al. | 2/209 |
| 3,918,098 | 11/1975 | Devaney et al. | 2/209 |
| 4,130,336 | 12/1978 | Dozier | 339/129 RS |

FOREIGN PATENT DOCUMENTS 552405 10/1941 United Kingdom ................ 403/133

Primary Examiner—Werner H. Schroeder
Assistant Examiner—Mary A. Ellis

[57] ABSTRACT

There is disclosed an acoustic earmuff device wherein there is provided an articulated earmuff-to-headband attachment construction which is readily fabricated and assembled and which provides sufficient freedom of pivotal motion of the earmuff relative to the headband as to allow each earmuff to readily assume the proper wearing position with respect to the head of the user. The invention utilizes a soft resilient grommet fitted through an aperture in the back wall of a rigid earcup to articulatingly capture a rigid stud extending inwardly from an end portion of a resilient headband.

10 Claims, 2 Drawing Figures

ARTICULATED EARMUFF-TO-HEADBAND ATTACHMENT CONSTRUCTION

BACKGROUND OF THE INVENTION

1. Field of the Invention

The present invention relates generally to acoustic earmuff devices and is more particularly concerned with a novel articulated earmuff-to-headband attachment construction therefor.

For purposes of the present invention an "acoustic earmuff device" is intended to mean a device broadly comprising a generally U-shaped resilient headband to the interior of each free end portion of which there is affixed an earmuff comprising a rigid earcup element. Such devices find applications as hearing protectors for workers in noisy environments and, when at least one earmuff is equipped with a suitable electromechanical transducer, or sound conducting tube, as earphone elements of communication systems. The resilient headband is generally adapted, such as by appropriate sizing design and selection of materials of construction thereof, to bias the earmuffs against the head of the wearer, thereby to secure them thereto. In view of the variable head sizes and shapes encountered in the user population, it is desirable to provide an earmuff-to-headband attachment construction which is pivotally articulated so as to allow the earmuffs to conform to the head shape of any user under the urging of the headband and to thereby effectuate a competent sealing engagement of the open ends of the earmuffs to the head. It is also desirable to provide the articulated attachment construction with sufficient range of motion as to allow the acoustic earmuff device to be worn with good effect with the headband in any of the over-the-head, behind-the-neck or below-the-chin positions.

2. Description of the Prior Art

The prior art discloses several types of articulated earmuff-to-headband attachment constructions which serve the aforementioned purposes to a greater or lesser degree. In British Patent Specification No. 1,347,824, published Feb. 27, 1974, to Exel Oy, there is disclosed a ball joint arrangement for adjusting the inclination of each earmuff relative to the headband. The ball element of the joint is contained in a spherical socket formed in the interior of the back wall of the earcup element of the earmuff. A stub extending inwardly from an end portion of the headband traverses an external aperture in the back wall of the earcup and is fitted into that portion of the ball exposed to the exterior of the earcup. The ball is secured into the internal spherical socket of the earcup back wall by means of an internal plug and star washer combination. While the earmuff-to-headband attachment construction of this patent publication appears to result in a good range of articulation of the earmuff relative to the headband, it is a somewhat complicated construction in terms of its fabrication and assembly and, moreover, does not result in acoustic isolation of the headband from the earmuff. Thus, sound wave or vibrational energy imparted from the external environment to the headband appears to be susceptible of conduction into the earcup elements through the disclosed ball joint construction.

In British Patent Specification No. 1,355,052, published May 30, 1974, to Robert Ian Johnson et al., there is disclosed a hearing protector comprising a pair of resilient, ear-insertable, one-piece, multiply-flanged earplugs affixed to inwardly directed ends of a resilient, generally U-shaped tubular headband. FIG. 4 and in the text relevant thereto disclose a direct swivelling attachment of each earplug to the headband comprising a ball-shaped inwardly directed free end of the headband fitted into a receiving socket formed in the outboard end of the earplug. FIG. 6 and the text relevant thereto disclose an attachment of the earplugs to the headband comprising a rigid connecting piece interposed between the headband and earplug, said connecting piece having a cylindrical outboard end of a dimension adapted to be tightly and rigidly fitted within a tubular inwardly turned free end of the headband and a double-barbed inboard end which is engaged within a socket provided in the outboard end of the earplug. The association between the earplugs and the headband in the construction of FIG. 6 is not said to be articulated and it does not appear to be susceptible of such character because the outboard end of the intermediate connecting piece is tightly affixed into the tubular end of the headband and because the linearly separated dual barbs of the inboard end of the connecting piece are both shown to be tightly captured in the resilient outboard socket of the earplug. Moreover, the various constructions of this publication are said to serve the principal function of urging the earplugs into the external auditory meatuses of the wearer under the influence of the headband. In the case of acoustic earmuff devices of the type concerned in the present invention, however, there is no invasive entry of any portion of the device into the ears of the user.

West German Patentschrift DE No. 25 16 709, laid open on Oct. 28, 1976, to Erwin Martin Heberer, discloses a ball-and-socket type attachment of acoustic earmuffs to a resilient headband. The ball element of the attachment is defined at the free inboard end of an inwardly directed stud affixed to the end of the headband. The socket element of the joint is contained in an externally tapered collet which comprises a plurality of split fingers at the outboard end thereof. Said fingers are sprung open and the ball inserted into the socket lying thereunder. Once the ball has been so inserted and seated within the outboard end of the collet, the inboard end thereof, which is multiply slotted and externally toothed, is forced into a close fitting tapered collet seat formed through the back wall of the earcup element of the earmuff, the external teeth of the collet splaying open upon entry of the inboard end thereof into the earcup chamber and thereby conjointly locking the collet into place within the tapered collet seat and securing the ball within socket underlying the outboard fingers of the collet. While the particular attachment construction disclosed in West German Patentschrift DE No. 25 16 709 appears to provide for good articulation between the earmuffs and the headband, said construction appears to suffer from a lack of acoustic isolation between the headband and the earmuffs. The headband, earcups and collet elements of the construction all appear to be composed of rigid sound conductive materials and are in physical contact in the assembled condition of the construction. Therefore, sound or vibrational energy which may be imparted to the headband from the external environment is provided with a conductive pathway into the rigid earcup elements of the construction.

In accordance with the present invention, there is provided a novel pivotally articulated earmuff-to-headband attachment construction having the attibutes, severally or in combination, of: simplicity of design, ease of fabrication, ease of assembly, pivotal articulation of sufficient range as to allow the earmuffs of acoustic earmuff devices so equipped to readily conform to the head of the user and which construction additionally provides substantial acoustic isolation of the earmuffs from the headband. Other benefits and advantages of the present invention will in part be obvious and will in part appear hereinafter.

SUMMARY OF THE INVENTION

In accordance with the invention there is provided a generally U-shaped resilient headband having an inwardly directed rigid stud affixed to each end portion thereof, said studs each being defined by an outboard shaft portion affixed to an end portion of the headband and an expanded free end inboard portion of larger diameter than said shaft portion. The acoustic earmuffs employed in the construction of the invention each comprise a rigid earcup element, the back wall of which comprises a generally centrally located aperture therethrough. The linking element of the articulated earmuff-to-headband attachment comprises a grommet composed of a soft resilient material, said grommet defining a hollow internal bore to receive the stud of the headband and comprising an external circumferential groove to receive the edge of the aperture of the earcup. The diameter of the grommet taken at the bottom of the groove is somewhat greater than the diameter of the receiving aperture of the earcup element, thereby to cause deformation of the grommet material underlying the groove and to produce an indwelling ridge within the internal bore thereof of smaller diameter than that of the expanded free end portion of said stud.

DESCRIPTION OF THE PREFERRED EMBODIMENT(S)

Figure 1:
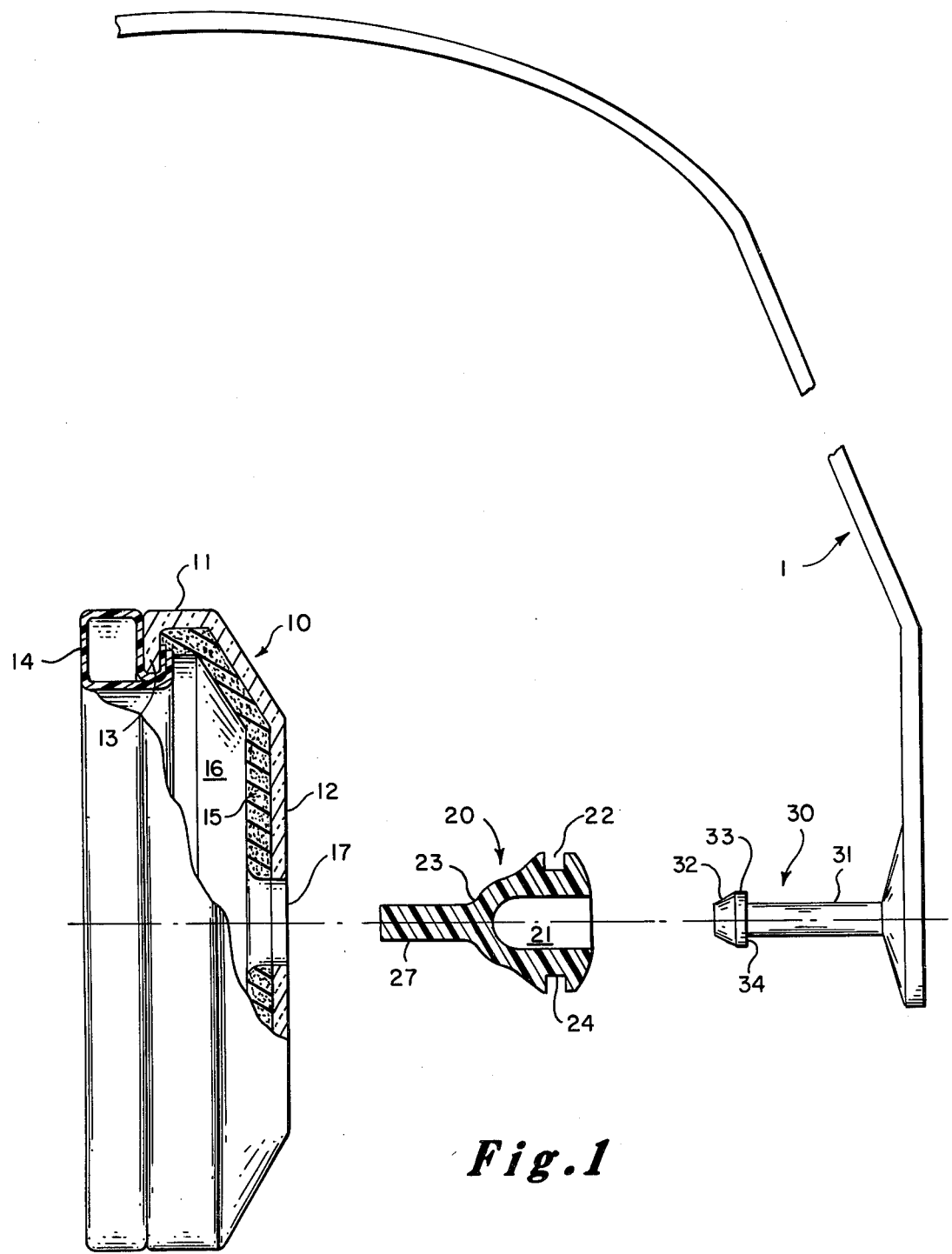
FIG. 1 hereof is a schematic, diagrammatic, partially sectional, exploded front view of a portion of an acoustic earmuff device in accordance with the invention.

Referring now to the drawing, wherein like reference numerals refer to like structures, the acoustic earmuff device of the invention broadly comprises a generally U-shaped, resilient headband (1) having articulatingly attached to the interior of each free end portion thereof an acoustic earmuff (10).

Resilient headband (1) constructions are well known and, therefore, require little further discussion herein. Suffice it to say, therefore, that the headband (1) is composed of or is of such construction as to provide it with a certain resilience when the open end of the "U" is splayed apart to fit the earmuff device to the head of the user, thereafter the recovery forces generated in the strained headband serving to bias the earmuff(s) inwardly and to foster secure attachment and good acoustic sealing of said earmuff(s) (10) to the user's head. Thus, suitable materials of construction for the headband (1) can comprise various thermoplastic or metallic materials such as spring steel, copper-beryllium alloys of fiber reinforced polymers which when suitably conformed, result in a resilient or springy construction. Desirably, the headband (1) of the invention will be of such construction as to provide the capability for adjustment of its overall length. Such-adjustable length resilient headband constructions are well known in the art and may include such design features as: (a) a pair of overlapping sliding members having means to maintain said members in alignment and means to secure the overlapped portions thereof upon completion of adjustment of the overall length thereof; (b) a pair of telescoping nested members having means to secure the nested portions thereof together upon completion of adjustment of the overall length thereof; and (c) separate end portion members for a central headband member of fixed length and comprising cooperative rack-and-pinion, toothed, interrupted thread or other means whereby each said end portion may be separately adjusted relative to the central headband member and thereafter secured at the adjusted length thereof. Further details concerning various exemplary adjustable-length resilient headband constructions may be had by reference to such literature as the aforementioned British Patent Specification No. 1,347,824 and West German Patentschrift No. 25 16 709, as well as to U.S. Pat. No. 1,167,368, Jan. 4, 1916, to C. Adams-Randall.

The acoustic earmuff (10) construction of the invention is generally conventional in nature and comprises a rigid earcup element (11) having a back wall (12). The rigid earcup element (11) may also beneficially comprise a retroverted continuous flange (13) extending inwardly and generally transversely from the circumference of the open end thereof and to which flange (13) there is affixed a suitable soft sealing element (14). Desirably, the interior of the rigid earcup element (11) comprises a liner (15) composed of a sound absorbing material such as an open-cell polymer foam.

The foregoing detailed discussions of the headband (1) and earmuff (10) elements of the acoustic earmuff device of the invention have thus far involved only those design parameters which are broadly conventional in the art of acoustic earmuff design. Therefore, turning now to the details of the articulated earmuff-to-headband attachment construction of the present invention, the basic elements thereof are: an aperture (17) located on the back wall (12) of rigid earcup element (11); a resilient grommet (20) defining a hollow internal bore (21) and a rigid stud (30) firmly affixed to a free end portion of headband (1) and extending inwardly therefrom.

Stud (30), as mentioned, is affixed to a free end portion of the headband (1) and is directed inwardly therefrom. The stud (30), in accordance with the invention, is of substantially rigid construction and comprises an outboard shaft portion (31) and an expanded free end inboard portion (32) of greater diameter than said shaft portion (31). The expanded free end inboard portion (32) of the stud (30) can take substantially any symmetrical geometric form such as, for instance, the form of a sphere or ball. However, we prefer the geometry of the expanded free end inboard portion (32) to take the form of a single blunt terminal barb whose greatest diameter is defined by a shoulder (33) of constant diameter located at the outboard end portion thereof and which further comprises an essentially flat outboard wall (34) extending inwardly from the outboard edge of said shoulder (33) and transversely to the longitudinal axis of the stud (30).

Grommet (20) is composed of a soft resilient elastomeric or plastomeric material and comprises an external circumferential groove (22) which is sized to receive the edge of aperture (17) therein. Desirably, although not necessarily, the grommet (20) will take the general form of a closed-ended thimble, the closed end (23) thereof defining the inboard end. The preferred thimble form of the grommet (20) provides the completed assembly of the invention (FIG. 2) with a closed inboard chamber (26) which serves as an acoustic barrier to the transmission of sound from the stud (30) into the interior space (16) of earmuff (10) and which also provides the capability for the use of a compatible lubricant fluid or grease within internal bore (21) without danger of migration of such lubricant into said interior space (16). Where the grommet (20) takes the preferred general form of a thimble, it is further preferred (as shown in FIG. 1) that there also be provided a sacrificial pull tab (27) extending longitudinally from the bottom (23) thereof, said tab (27) being of substantially smaller diameter than the aperture (17) of earcup element (11). Said tab (27) is useful in facilitating assembly of the grommet (20) to the earcup element (11) as will be described more fully hereinafter.

Figure 2:
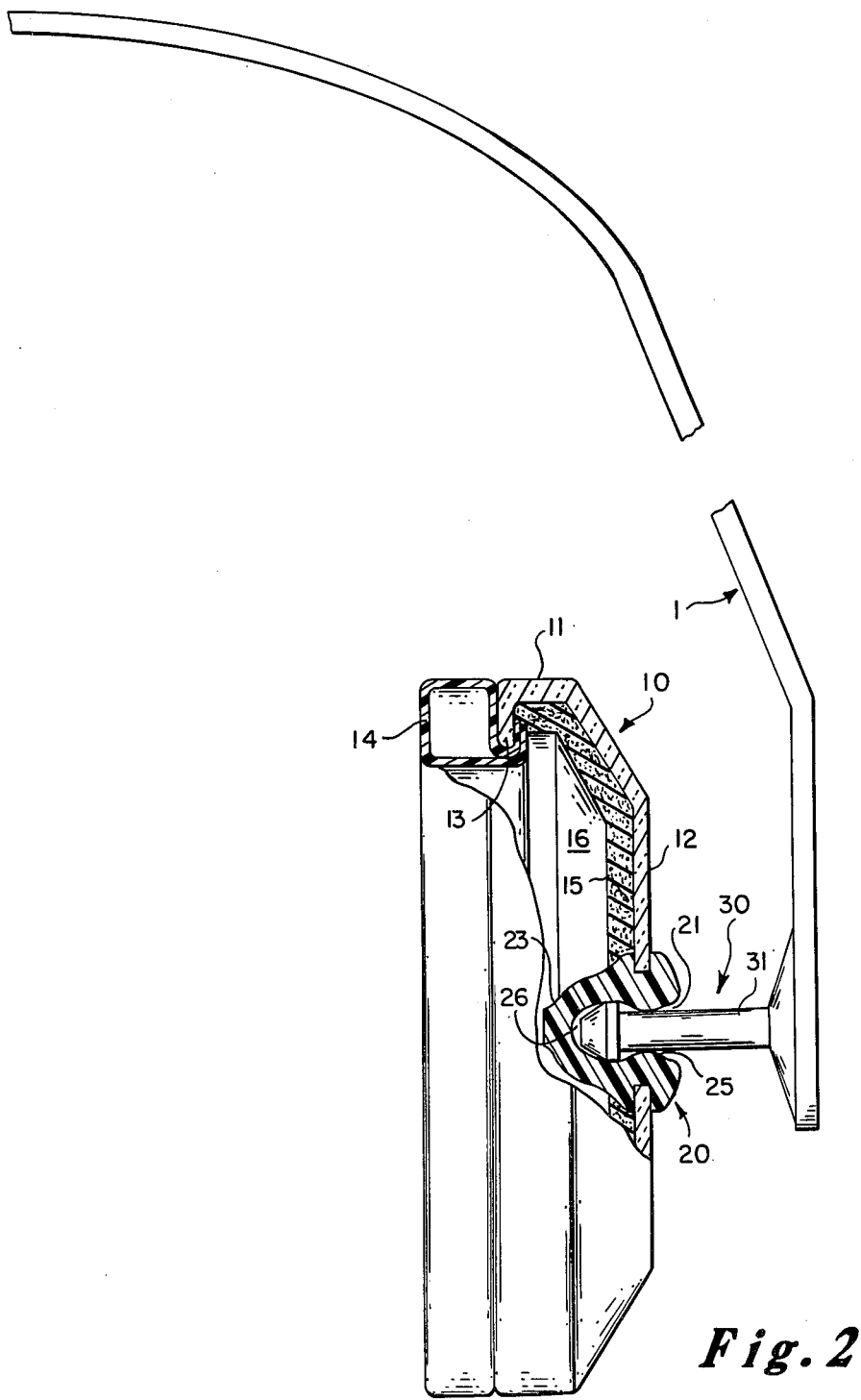
FIG. 2 hereof is a schematic, diagrammatic, partially sectional, front assembled view of that portion of the acoustic earmuff device of the invention shown in FIG. 1.

As will be particularly noted from the assembled construction of FIG. 2, the grommet (20) provides substantial acoustic decoupling of the rigid stud (30) and headband (1) from the rigid earcup element (11) since the soft resilient material of the grommet (20) is fully interposed between the stud (30) and earcup (11) elements. This is particularly so where the soft resilient material of construction of the grommet (20) has a Shore A Durometer hardness value (ASTM D2240-81) of no greater than 80 and, preferably, of no greater than about 60. Various elastometric and plastomeric materials can be employed in the grommet (20) construction such as butyl rubber, butadiene rubber, silicone rubber, polyurethane elastomers, natural rubber, ethylene-vinyl acetate copolymers, polyvinylidene chloride, polyvinylchloride homopolymers and copolymers and the like. Particularly preferred is a thermoplastic styrene-butadiene-rubber block copolymer. Such SBR block copolymers are readily formed into complex shapes by standard thermoplastic polymer molding techniques. An example of a commercially available thermoplastic SBR block copolymer material found useful in the practice of the invention is KRATON G-2705, produced by Shell Chemical Company, Synthetic Rubber Division, N.Y., N.Y. This material has a Shore A Durometer hardness value (ASTM D2240-81) of about 45.

As shown in FIGS. 1 and 2, the diameter of aperture (17) is somewhat smaller that the diameter of the grommet (20) taken at the bottom (24) of groove (22), the edge of said aperture (17) thus bearing on said bottom (24) and inwardly deforming the resilient material underlying the groove (22), thereby to cause a corresponding indwelling continuous ridge (25) of lesser diameter than the maximum diameter of the expanded free end inboard portion (32) of stud (30) to be formed within the internal bore (21) of grommet (20). Accordingly, the narrowing of the internal bore (21) caused by the action of the edge of aperture (17) acting against the bottom (24) of groove (22) is of sufficient magnitude as to cause the resulting indwelling ridge (25) to lockingly capture the expanded free end inboard portion (32) of stud (30) on the inboard side of said ridge (25) while maintaining freedom of motion of the shaft (31) of stud (30) therewithin.

In assembling the articulated earmuff-to-headband attachment construction of the invention, the pull tab (27) (FIG. 1) of grommet (20) is inserted into the aperture (17) of rigid earcup element (11) and pulled from the interior of said earcup element until the grommet (20) advances into the aperture (17) to the extent that groove (22) becomes seated over the edge of said aperture (17). Pull tab (27) is then clipped or otherwise removed close to the bottom (23) of the grommet (20) (FIG. 2). Finally, the expanded free end inboard portion (32) of stud (30), which may be preliminarily lubricated, is inserted into the bore (21) of grommet (20) and the stud forced into said bore (21) to the point that said expanded free end portion (32) passes inboard of the indwelling ridge (25).

Utilizing the preferred blunt barb form of the expanded free end inboard portion (32), it will be seen that the leading or divergent surfaces of the barb serve to non-injuriously cam the material of the indwelling ridge (25) outwardly and that, upon passage of the barb through the indwelling ridge (25), the sharp outboard corner of the barb defined at the junction of the shoulder (33) and outboard wall (34) thereafter prevents retrograde or removal motion of the barb from within the grommet (20).

From the foregoing description it can be seen that the relative dimensioning of various of the elements of the construction of the invention can be of importance. Accordingly, the following general dimensional guidelines should be observed.

Aperture (17) should be of sufficiently large diameter as to allow the expanded free end inboard portion (32) of stud (30) to pass freely therethrough.

The diameter of aperture (17), the diameter of the grommet (20) taken at the bottom (24) of circumferential groove (22) and the wall thickness of the grommet (20) underlying the groove (22) should be selected such as to cause the indwelling ridge (25) formed within the internal bore (21) of grommet (20) to be of sufficiently small diameter as to lockingly secure the expanded free end inboard portion (32) of stud (30) to the inboard side of ridge (25). Preferably, these dimensions will also be selected such that the diameter of the indwelling ridge (25) will be sufficiently large that the expanded free end inboard portion (32) of the stud (30) may, if so desired, be forcefully extracted from its capture by said indwelling ridge (25) without physical trauma being done to any of the elements of the construction. This is a desirable feature in that it allows user servicing or replacement of one or both earmuff(s) (10) or of the headband(1).

Where the preferred thimble form of grommet (20) is employed in the practice of the invention it is an even further desideratum that the diameter of the internal bore (21) inboard of the indwelling ridge (25) and the diameter of the expanded free end inboard portion (32) of stud (30) be selected such that there results a light interference fit of said expanded free end inboard portion (32) within said inboard portion of internal bore (21). By this association there results a natural resting or "no-load" positioning of the stud (30) relative to the earcup element (11) and displacement motion of the stud (30) from this natural resting position will be lightly resisted by the resilient material of the inboard portion of internal bore (21) acting against the expanded free end inboard portion (32) of the stud (30). For reasons not yet fully understood, the foregoing structural association and the accompanying light resistance to displacement of the stud (30) from its natural positioning within the grommet (20) tends to mitigate against the deleterious phenomenon of raising of the front edge of the acoustic earmuff (10) from the head of the user when the resilient headband (1) is worn in the behind-the-neck position. this phenomenon, depending somewhat upon the size and/or geometry of the head of the particular wearer, can often occur utilizing acoustic earmuff devices equipped with articulated earmuff-to-headband constructions of the prior art and is generally reflected in Noise Reduction Rating values (per ANSI Test Procedure S3.19-1975) for such earmuff devices which are substantially lower when the headbands thereof are worn in the behind-the-neck position as compared to the NRR values attained when the headbands are worn in the over-the-head position. It is pointed out that the NRR values arising from the practice of the ANSI Test Procedure S3.19-1975 are weighed average values utilizing a statistically meaningful number of human test subjects.

As an example of the above-described principles of dimensioning of the elements of the invention, it has been found that one suitable construction of the invention is provided by the following combination of elements Earcup element (11) is composed of injection molded polyvinylchloride, has a back wall (12) thickness of 3.18mm (0.125 inch) and comprises an aperture (17) having a diameter of 12.7 mm (0.500 inch) located centrally on said back wall (12).

Grommet (20), of closed-ended thimble shape conforming generally to the depiction thereof shown in the drawing hereof, is molded of KRATON G-2705, a thermoplastic SBR block copolymer, and has an unconstrained internal bore (21) diameter of 8.1 mm (0.320 inch), a circumferential external groove (22) having a depth of 2.55 mm (0.100 inch ), a width of 3.1 mm (0.122 inch) and a diameter taken at the bottom (24) thereof of 15.2 mm (0.598 inch), thereby providing an underlying wall thickness at the locus of said groove (22) of 3.55 mm (0.139 inch). Pull tab (27) has a diameter of 5.1 mm (0.200 inch) and is removed after assembly of grommet (20) to earcup element (11), the overall length of the remaining grommet (20) being about 19.1 mm (0.750 inch).

Stud (30) is formed of glass filled nylon and has an overall length of 17.8 mm (0.7 inch). Cylindrical shaft portion (31) has a length of 11.4 mm (0.45 inch) and a diameter of 6.35 mm (0.250 inch). Expanded free end inboard portion (32) is of single blunt barb configuration and has an overall length of 3.8 mm (0.15 inch), and a constant diameter outboard shoulder (33) having a length of 1.9 mm (0.75 inch) and a diameter of 8.13 mm (0.320 inch). The stud (30) is molded integrally with headband (1), which is of similar composition.

It should be noted and understood that the specific dimensions, geometries and materials given above are only illustrative in nature and are not to be construed as limiting of the invention. Bearing in mind the principles of design and operations set forth hereinbefore, variations and modifications of the invention may be made which are obvious to those skilled in the art without departing from the essential scope and spirit of the invention.

The embodiments of the invention in which an exclusive property or privilege is claimed are defined in the following claims:

1. An articulated earmuff-to-headband construction for acoustic earmuff devices which comprises:

a rigid stud having an outboard shaft portion for interiorly directed fixation to an end portion of a resilient headband and an expanded free end inboard portion of substantially greater maximum diameter than said shaft portion;

an acoustic earmuff comprising a rigid earcup element having a back wall, said back wall having an aperture therethrough; and a grommet composed of a soft resilient material and comprising (a) a internal bore, the diameter of said bore, in the unconstructed state, being not substantially less than the maximum diameter of said expanded free end inboard portion of said stud, and (b) a circumferential external groove of a size and shape to receive said aperture of said earcup;

the diameter of said aperture being sufficiently less than the diameter of said grommet taken at the bottom of said groove such that, upon said receiving of said aperture in said groove, the material of said grommet underlying said groove is inwardly deformed to define an indwelling ridge on said internal bore of sufficiently lesser diameter than the maximum diameter of said expanded free end inboard portion of said stud as to lockingly and articulatingly capture said stud with said expanded free end inboard portion thereof being inboard of said ridge.

2. The construction of claim 1 wherein said grommet is composed of material having a Shore A Durometer hardness value of no greater than about 60.

3. The construction of claim 1 wherein said grommet is composed of a thermoplastic styrene-butadiene-rubber block copolymer.

4. The construction of claim 1 wherein said grommet takes the general form of a closed-ended thimble, the closed end of said thimble defining the inboard end thereof.

5. The construction of claim 4 wherein the exterior of said closed end of said thimble form grommet comprises a removable pull tab extending therefrom, said tab being of substantially smaller diameter than said aperture.

6. The construction of claim 4 comprising a compatible lubricant within said thimble.

7. The construction of claim 4 wherein the internal bore of said thimble form grommet inboard of said groove and said expanded free end inboard portion of said stud are in light interference fit relationship.

8. The construction of claim 1 wherein said expanded free end inboard portion of said stud has the shape of a single blunt barb.

9. The construction of claim 8 wherein said barb-shaped expanded free end inboard portion of said stud comprises an outboard shoulder portion of constant maximum diameter.

10. The construction of claim 9 wherein said barb-shaped expanded free end inboard portion of said stud comprises an essentially flat outboard wall extending inwardly from the outboard end of said shoulder, transversely to the longitudinal axis of said stud.

* * * * *

UNITED STATES PATENT AND TRADEMARK OFFICE
CERTIFICATE OF CORRECTION

PATENT NO. : 4,471,496

DATED : September 18, 1984

INVENTOR(S) : Ross Gardner, Jr., Robert Falco

It is certified that error appears in the above—identified patent and that said Letters Patent is hereby corrected as shown below:

```
Col. 2, l. 67, "attibutes" should read -- attributes --.
Col. 3, l. 65, "of" should read -- or --.
Col. 7, l. 2, "this" should read -- This --.
Claim 1, line 16, "unconstructed" should read -- unconstrained --
```

Signed and Sealed this

Second Day of July 1985

[SEAL]

Attest:

DONALD J. QUIGG

Attesting Officer     Acting Commissioner of Patents and Trademarks